United States Patent [19]

Huitema

[11] Patent Number: 5,361,583
[45] Date of Patent: Nov. 8, 1994

[54] PRESSURIZED FLUID ACTUATION SYSTEM WITH VARIABLE FORCE AND STROKE OUTPUT FOR USE IN A SURGICAL INSTRUMENT

[75] Inventor: Thomas W. Huitema, Cincinnati, Ohio

[73] Assignee: Ethicon, Inc., Cincinnati, Ohio

[21] Appl. No.: 129,976

[22] Filed: Sep. 30, 1993

[51] Int. Cl.$^5$ .................. F16D 31/02; A61B 17/42
[52] U.S. Cl. ........................... 60/413; 60/478; 606/51; 606/131; 606/205
[58] Field of Search ............ 60/407, 372, 408, 410, 60/413, 477, 478; 606/51, 52, 131, 133, 205, 206, 207, 208, 209, 210, 211

[56] References Cited

U.S. PATENT DOCUMENTS

| | | | |
|---|---|---|---|
| 1,991,816 | 2/1935 | Moseley | 606/133 |
| 3,266,494 | 8/1966 | Brownrigg et al. | 606/206 |
| 4,171,701 | 10/1979 | Walter et al. | 606/133 X |
| 4,485,817 | 12/1984 | Swiggett . | |
| 4,488,523 | 10/1984 | Shichman . | |
| 4,721,099 | 1/1988 | Chikama . | |
| 4,815,450 | 3/1989 | Patel . | |
| 4,832,473 | 5/1989 | Ueda . | |
| 4,890,602 | 1/1990 | Hake . | |
| 4,893,613 | 1/1990 | Hake . | |
| 5,050,380 | 9/1991 | Jonsson | 60/413 |
| 5,080,000 | 1/1992 | Bubic . | |
| 5,179,934 | 1/1993 | Nagayoshi et al. . | |
| 5,258,006 | 11/1993 | Rydell et al. | 606/205 |
| 5,276,306 | 1/1994 | Huffman | 606/131 X |

OTHER PUBLICATIONS

U.S. patent application Ser. No. 08/130,068 entitled "Articulable Socket Joint Assembly For An Endoscopic Instrument And Surgical Fastener Track Therefor." F.D.: Sep. 30, 1993.

U.S. patent application Ser. No. 08/129,649 entitled "Pressurized Fluid Actuation System For Amplifying Operator Input Force In A Surgical Instrument." F.D.: Sep. 30, 1993.

U.S. patent application Ser. No. 08/130,065. filing date: Sep. 30, 1993.

Primary Examiner—Edward K. Look
Assistant Examiner—Hoang Nguyen
Attorney, Agent, or Firm—Dressler, Goldsmith, Shore & Milnamow, Ltd.

[57] ABSTRACT

A surgical instrument actuation system is provided with a double-acting fluid pressure piston pump and a double-acting fluid actuator. An operating member is connected to the pump piston, and a two-position directional valve communicates between the pump and actuator. A valve actuator means is responsive to the pump pressure or to the position of the pump piston or actuator piston. This switches the valve from the first position to the second position so that the system operates to apply a higher actuator force at a lower stroking speed.

13 Claims, 6 Drawing Sheets

PRESSURIZED FLUID ACTUATION SYSTEM WITH VARIABLE FORCE AND STROKE OUTPUT FOR USE IN A SURGICAL INSTRUMENT

TECHNICAL FIELD

This invention relates generally to an actuation system for surgical instruments, including instruments used in endoscopic procedures as well as in open surgery procedures. This system is particularly suitable for incorporation in a ligating clip applier.

BACKGROUND OF THE INVENTION AND TECHNICAL PROBLEMS POSED BY THE PRIOR ART

A variety of designs have been commercialized or proposed for instruments incorporating a pair of cooperating jaws (i.e., a jaw assembly) in which one or both jaws pivot or otherwise move between open and closed positions. Examples of such instruments include tissue graspers, tissue clamps, needle graspers, tissue cutters, linear staplers, ligating clip appliers, and the like.

In some surgical applications, it is necessary or advantageous to apply relatively high squeezing forces. Thus, it would be desirable to provide an improved actuation system with an amplification capability for increasing the jaw closure force compared to the operator input force. It would also be beneficial if the system could accommodate designs wherein the closure force can be varied during the closure stroke.

For example, when an open ligating clip is squeezed closed about tissue by means of jaws on a ligating clip applier, the initially open legs of the clip at first offer little resistance to the closing force. Only a relatively low compression force need be initially applied to each leg of the clip to pivot or deform the legs through a major portion of the leg travel. However, as the ligating clip legs compress the tissue and approach the fully closed configuration, the magnitude of the force required to continue moving the clip legs together can increase substantially. Accordingly, it would be desirable to provide a ligating clip jaw closure actuation system which could accommodate the increasing closure force that occurs with increasing jaw travel.

It would also be beneficial to provide an improved actuation system which could be substantially automatically responsive to an increased load and provide an increased actuator force in response.

In various surgical procedures, it is sometimes desirable to insure that a surgical instrument, once it has begun operation (e.g., closing a clip about tissue), continue that operation to completion rather than interrupt and prematurely terminate the operation. To this end, it would be advantageous if an improved actuation system could be provided with an anti-backup design. However, in some situations it may nevertheless desirable to knowingly terminate the instrument operation prior to completion of the instrument cycle. Thus, it would be beneficial to provide an improved actuation system that could accommodate the release or avoidance of the anti-backup feature.

It would further be desirable to provide an improved actuation system having a reduced number of components, such as mechanical linkages, rachet mechanisms, and the like, so as to reduce the number of components and so as to minimize friction losses.

Finally, it would also be beneficial if such an improved system could be provided with sufficient capacity and strength to accommodate relatively high loads during operation of the instrument.

The present invention provides an improved actuation system which can be used to operate a surgical instrument and which can accommodate designs having the above-discussed benefits and features.

SUMMARY OF THE INVENTION

According to the principles of the present invention, a pressurized fluid actuation system is provided for moving an endoscopic or open surgical procedure instrument component. The system includes a double-acting fluid actuator defining an extension chamber and a retraction chamber separated by a piston for engaging the component.

A double-acting fluid pressure piston pump defines a pressurizing chamber and a return chamber separated by a piston. The pump pressurizing chamber communicates with the actuator extension chamber.

An operating member is connected or mounted to the pump piston. A two-position, directional valve communicates in a first position between the pump pressurizing chamber and the actuator retraction chamber. The valve communicates in a second position between the pump return chamber and the actuator retraction chamber.

The system includes a valve actuation means which switches the valve in response to a sensed pressure of the pump piston or in response to the position of either the pump piston or the actuator piston. The valve is switched from the first position to the second position when either the pump piston or the actuator piston has moved to an intermediate location. The valve switches from the second position to the first position when the piston of either the pump or the actuator has returned from the intermediate position.

A pressurized fluid reservoir is connected to the pump return chamber through a check valve for preventing flow through the check valve into the reservoir. The pressurized fluid reservoir is also connected to the actuator extension chamber through a de-stroking valve. The de-stroking valve can be selectively opened to pass flow through it to the reservoir and can be closed to occlude the flow.

This novel system can provide a relatively large actuator output stroke for a given operator input stroke during an initial, major portion of the operating cycle when the output force requirements are low.

The system senses, or responds to an operating position corresponding to, an increase in the load. The system then shifts automatically to a mode in which a relatively large actuator output force is generated for a given operator input force during a final portion of the instrument operation cycle when the output force requirements are high but the output stroke requirement is relatively low.

The operation of the instrument cannot be reversed at intermediate cycle positions unless the de-stroking valve is operated to release the anti-backup feature.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same.

DESCRIPTION OF THE PREFERRED EMBODIMENTS

One aspect of the present invention relates to a fluid actuation system which can be employed to operate surgical instruments and which can be incorporated in a variety of designs providing unique operational characteristics and capabilities. The actuation system is especially suitable for use in a ligating clip applier instrument.

In addition, the actuation system can be employed in instruments for operating devices to effect a variety of functions with respect to the surgical site. Such functions can include, but are not limited to, grasping, clamping, and applying staples or ligating clips.

Various embodiments of the actuation system can be provided in an instrument with sufficient interior space to accommodate internal passages and components (e.g., sensor lines and components, conduits, fastener actuation systems, etc.).

Further, the actuation system of the present invention accommodates incorporation in instruments having various designs for venting or sealing the instruments, including the use of filters for filtering gas and smoke.

While this invention is susceptible of embodiment in many different forms, this specification and the accompanying drawings disclose only some specific forms as examples of the invention. The invention is not intended to be limited to the embodiments so described, however. The scope of the invention is pointed out in the appended claims.

For ease of description, the actuation system embodiments of this invention are described in various operating positions, and terms such as upper, lower, horizontal, etc., are used with reference to these positions. It will be understood, however, that the system components of this invention may be manufactured, stored, transported, used, and sold in an orientation other than the positions described.

Figures illustrating the actuation system show some mechanical elements that are known and that will be recognized by one skilled in the art. The detailed descriptions of such elements are not necessary to an understanding of the invention, and accordingly, are herein presented only to the degree necessary to facilitate an understanding of the novel features of the present invention.

The actuation system incorporating the present invention can be used in instruments that have certain conventional components the details of which, although not fully illustrated or described, will be apparent to those having skill in the art and an understanding of the necessary functions of such instrument components.

Figure 1:
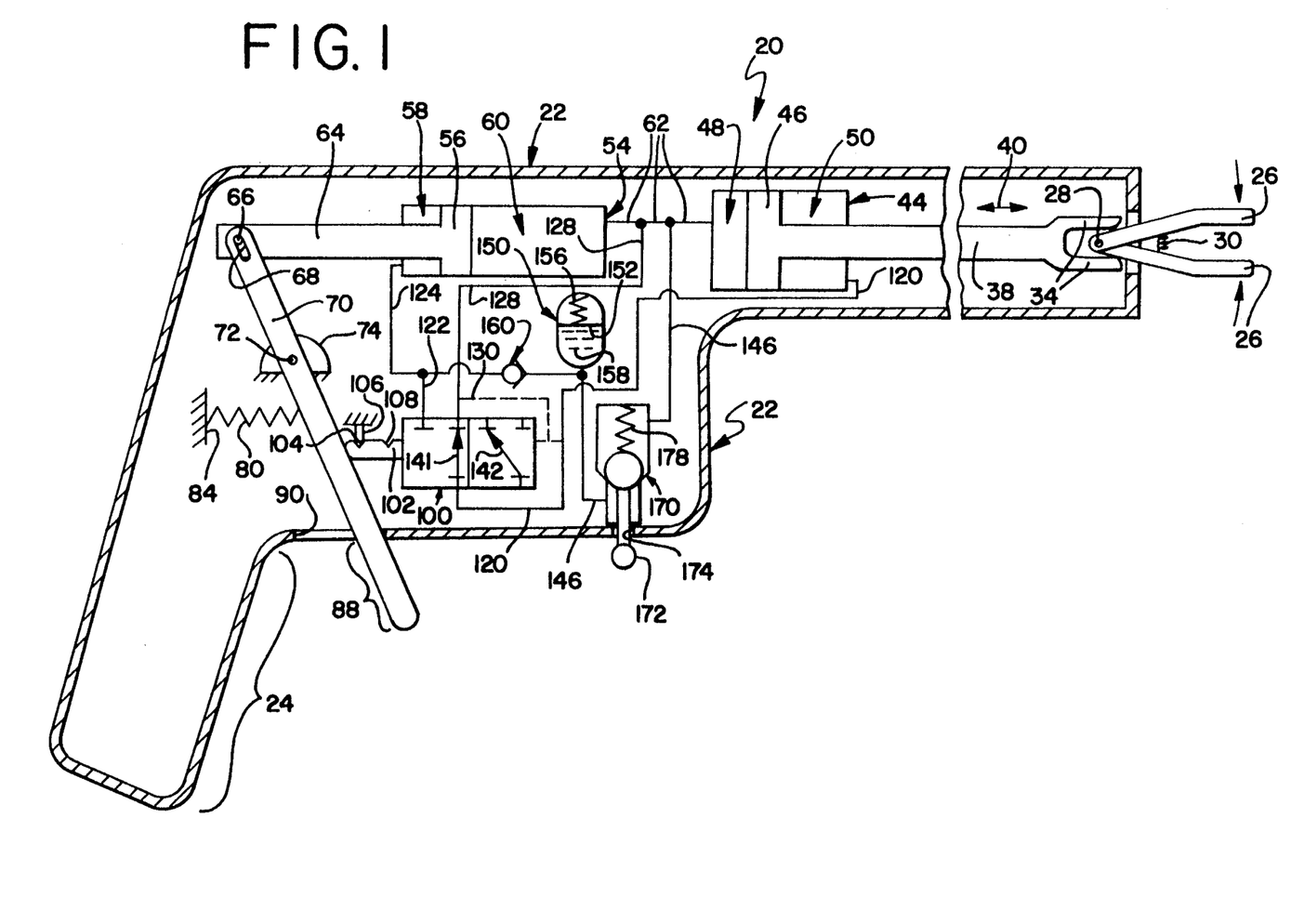
FIG. 1 is a simplified, partially diagrammatic, cross-sectional view of a surgical instrument incorporating a first embodiment of the fluid actuation system of the present invention which is schematically illustrated in a hydraulic circuit diagram.

FIGS. 1–5 schematically illustrate some basic features of a first embodiment of the actuation system of the present invention. The system is adapted to be incorporated in an open surgery or endoscopic instrument 20, and part of the instrument may typically include a support housing 22 (FIG. 1). The instrument 20 preferably has a pistol grip handle 24 which is grasped by the surgeon. In an endoscopic instrument, a proximal part of the housing 22 remains outside of the patient while the rest of the instrument is inserted through the trocar cannula (not illustrated) and into the body cavity.

The instrument 20 has a jaw assembly comprising a pair of jaws 26 which are pivotally mounted to the housing on a pin 28. The jaws 26 are normally biased outwardly to an open position by a spring 30. The jaws 26 are forced closer together, to a closed position, when engaged by a forwardly moving cam channel 34 at the end of an actuator rod 38.

The assembly of the jaws 26 and the cam channel 34 is diagrammatically illustrated for simplicity in FIG. 1, and the specific detailed designs of such components form no part of the present invention. Such a jaw assembly may be employed for grasping tissue or for applying a ligating clip (not illustrated) to tissue, such as to a blood vessel. Depending upon the actual structure of the jaw assembly, a plurality of ligating clips or other fasteners could be applied simultaneously or seriatim.

Instead of a jaw assembly, the distal end of the instrument 20 could be provided with other components or end effectors such as tissue cutters, staplers, and the like. Indeed, the end effector could include a needle or probe-like member for longitudinal movement in response to movement of the rod 38 in either of the opposite directions illustrated by the double headed arrow 40.

The rod 38 is operated by a double-acting fluid actuator 44. The rod 38 extends into the actuator housing or cylinder and is connected to a piston 46 therein. The piston 46 separates an extension chamber 48 on one side from a retraction chamber 50 on the other side.

A double-acting fluid pressure piston pump 54 is provided to operate the actuator 44. The pump 54 includes a housing or cylinder slidably receiving a pump piston 56 which separates a pressurizing chamber 60 on one side from a return chamber 58 on the other side. The pump pressurizing chamber 60 communicates with the actuator extension chamber 48 through a line 62.

A piston rod 64 extends proximally or rearwardly from the pump piston 56. The rod carries a pin 66 engaged in a slot 68 defined in the upper end of an operating lever 70. The operating lever 70 is pivotally mounted on a pin 72 to a fixed portion of the housing schematically illustrated as a semi-cylindrical mounting block 74. The lever 70 is normally biased forwardly in the instrument 20 by a compression spring 80 which has one end engaging the lever 70 below the pivot mounting pin 72 and which has another end compressively engaging a stationary boss 84 in the housing. The lever 70 has a distal end 88 projecting downwardly through a slot 90 defined in the instrument housing 22.

A three port, two-position, directional valve 100 is mounted adjacent the lever 70. The valve 100 is adapted to be mechanically engaged by the lever 70 to shift the valve to a first position illustrated in FIG. 1 when the lever 70 is pivoted to one extreme of its range of movement (as illustrated in FIG. 1). To this end, the valve 100 includes a projecting actuation rod or stem 102 having a distal end adapted to be engaged by the lever 70.

Figure 4:
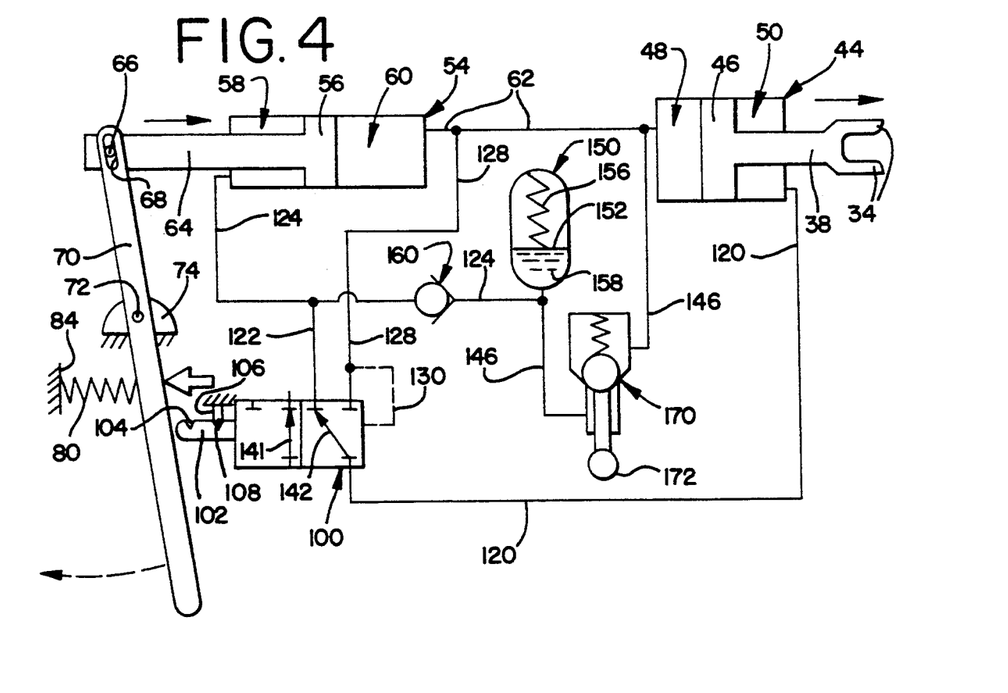

The valve rod or stem 102 defines a first notch 104 adapted to receive the distal end of a resilient, or spring-biased, tooth 106. The stem 102 also defines a second notch 108. When the valve 100 is in a second position (see FIGS. 4 and 5), the stem and notches are displaced (to the left as illustrated in FIG. 4) so that the second notch 108 is engaged by the tooth 106. The notches 104 and 108 and the tooth 106 function as a detent control to hold the directional valve 100 alternately in each of the first and second positions. Preferably, this detent control arrangement holds the valve in the first and second positions with a predetermined amount of force. Thus, the valve 100 will not move from the first position illustrated in FIG. 1 to the second position illustrated in FIG. 4 unless the predetermined amount of detent control force established by the engagement of the tooth 106 with the notch 104 is overcome (by a force tending to urge the valve 100 to the left as viewed in FIG. 1).

The valve 100 is connected to the actuator retraction chamber 50 through a line 120 and is connected to the pump 54 by a line 122 extending from the valve 100 which joins a line 124 extending into the pump return chamber 58.

The valve 100 is also connected to the pump pressurizing chamber 60 through a line 128. A pilot line 130 is connected from the valve 100 to the line 128 for communication with the pump pressurizing chamber 60. The pilot line 130 supplies pressure to switch the valve 100 from the first position (FIG. 1) to the second position (FIG. 4) when the pressure in the pump pressurizing chamber 60 exceeds a predetermined pressure sufficient to overcome the engagement force of the detent control (tooth 106 engaged with the valve notch 104 in FIG. 1).

When the directional valve 100 is in the first position illustrated in FIG. 1, a valve first passage 141 permits communication between the actuator retraction chamber 50 (through line 120 to passage 141) with the pump pressurizing chamber 60 (through the connection from the valve first passage 141 with the line 128 which communicates with line 62 connected to the pump pressurizing chamber 60). When the valve 100 is in the first position illustrated in FIG. 1, the line 122 at the valve 100 is blocked so that there is no communication through the valve from the pump return chamber 58.

When the valve 100 is in the second position illustrated in FIG. 4, the valve has a second passage 142 which establishes communication with the actuator retraction chamber 50 through line 120. Further, when the valve 100 is in the second position illustrated in FIG. 4, the valve second passage 142 communicates with the line 122 which is connected with line 124 extending to the pump return chamber 58. When the valve 100 is in the second position illustrated in FIG. 4, the valve occludes the line 128 which extends to the line 62 connected to the pump pressurizing chamber 60 and actuator extension chamber 48.

The pilot-actuated, directional valve 100 may be of any suitable conventional or special design which employs a pilot line (e.g., line 130) to switch the valve from a first position to a second position. The detailed design and operation of the internal port structure of such a pilot-actuated, two-position, directional valve forms no part of the present invention.

Figure 5:
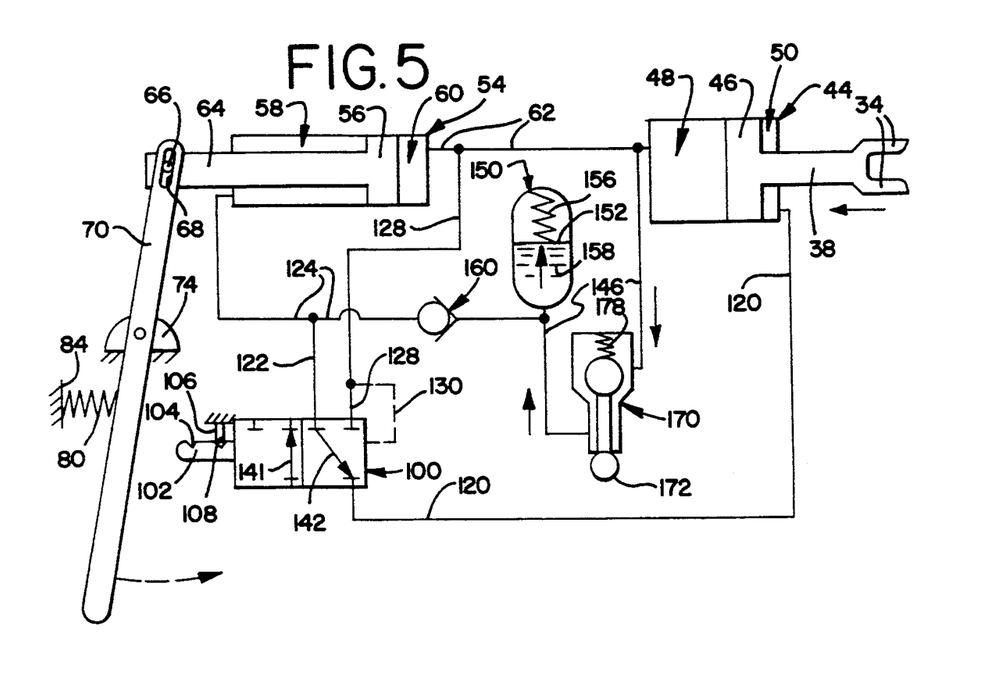

When the directional valve 100 is in the second position illustrated in FIGS. 4 and 5, it remains in that position until moved back to the first position (FIG. 1) in response to being mechanically engaged with the lever 70 which, when sufficient force is applied to it, can push the valve stem 102 so as to move the valve 100 back to the first position.

The line 124 extending from the pump return chamber 58 and from the valve connection line 122 communicates with a line 146 connected to a lightly pressurized fluid reservoir 150. The reservoir 150 is a unit containing a sealed diaphragm or membrane 152 normally biased toward one end of the reservoir by gas or by a compression spring 156. Hydraulic fluid 158 can accumulate in the reservoir on the side of the diaphragm 152 opposite the spring 156. In one contemplated design, the reservoir diaphragm maintains a pressure of about 15 psig on the fluid. The reservoir 150 may be of any suitable convention or special design, and the detail design of the reservoir 150 forms no part of the present invention.

A check valve 160 is provided in the line 124 between the pressurized fluid reservoir 150 and the connection to line 122 which extends to the directional valve 100. The check valve 160 may be of any suitable conventional or special design and the detailed construction of the check valve 160 forms no part of the present invention.

The line 146 connected to the pressurized fluid reservoir 150 extends to the line 62 which is connected to the actuator extension chamber 48 and pump pressurizing chamber 60. A de-stroking valve 170 is mounted in the line 146. The de-stroking valve 170 can be manually operated with a handle 172 projecting through an aperture 174 in the instrument housing 22 (FIG. 1). The de-stroking valve 170 is normally biased to a closed position by an internal spring 178. Thus, the de-stroking valve normally occludes the line 146. When the de-stroking valve handle 172 is pushed inwardly, the de-stroking valve is opened, and flow can pass through the de-stroking valve along the line 146. The de-stroking valve 170 may be of any suitable special or conventional design, and the detailed construction of such a valve forms no part of the present invention.

OPERATION OF THE SYSTEM

The sequential operation of the system is illustrated in FIGS. 2–5. The pump piston 56 is initially positioned near the fluid inlet end of the pump return chamber 58, and the actuator piston 46 is positioned near the fluid inlet end of the actuator extension chamber 46. With the directional valve 100 in the first position illustrated in FIG. 2, the system is in the "high speed, low load" mode or configuration. In this mode, the pump pressurizing chamber 60 communicates through line 128, valve 100, and line 120 with the actuator retraction chamber 50. At all times the pump pressurizing chamber 60 is also in direct communication through line 62 with the actuator extension chamber 48.

Figure 2:
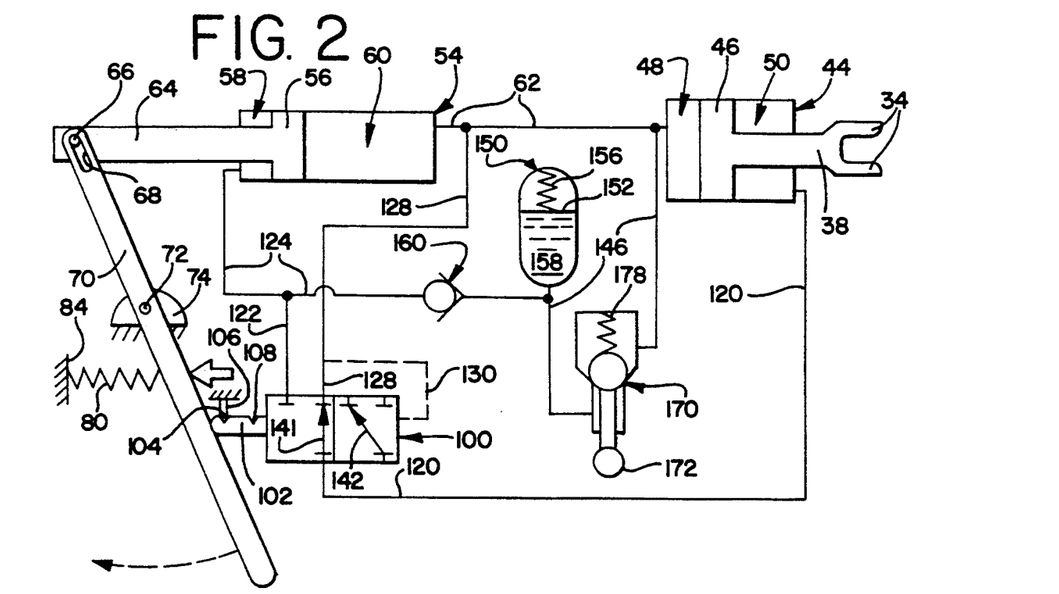
FIGS. 2–5 are schematic, hydraulic circuit diagrams of the fluid actuation system shown in FIG. 1, and FIGS. 2–5 sequentially illustrate the operation cycle of the system.

As the lever 70 is pivoted clockwise as viewed in FIG. 2, the pump piston 56 forces the hydraulic fluid out of the pump pressurizing chamber 60 to both sides of the actuator piston 46. The force on the actuator piston 46 is equal to the product of (1) the pressure and (2) the difference between the piston area facing the extension chamber 48 and the piston area facing the retraction chamber 50. The difference is the area occupied by the rod 38.

For example, assume that the surface of the actuator piston 46 facing the extension chamber 48 has an area of 3 in$^2$, that the cross-sectional area of the connection of the rod 38 to the piston 46 is 1.1 in.$^2$, and that the annular area of the actuator piston 46 (around the rod 38) which faces the retraction chamber 50 is 1.9 in.$^2$ Thus, the surface area of the actuator piston 46 facing the extension chamber 48 is 1.1 in.$^2$ greater than the piston area facing the retraction chamber 50.

For purposes of this illustrative example, we assume further that the surface area of the pump piston 56 facing the pressurizing chamber 60 is 2 in.$^2$, that the area of the connection of the rod 64 to the piston 56 is 0.667 in.$^2$, and that the area of the piston 56 around the rod 64 facing the return chamber 58 is 1.333 in.$^2$.

In this illustrative example, consider that the lever 70 is pivoted in a clockwise direction so as to move the pump piston 56 at a rate of 1 in./second. The output speed of the actuator piston 46 will then be (1 in.-/second×2 in.$^2$)/1.1 in.$^2$=1.82 in./second. This is nearly twice the 1 in./second input speed of the pump piston 56.

If the lever 70 is operated to apply a 100 lb. force to the pump piston 56, then the output force of the actuator 46 will be (100 lb./2 in.$^2$)×1.1 in.$^2$=55 lb.

The above described operating mode is desirable during the early stage of the operation of some instruments. Such a mode of operation is especially suitable for jaw closure devices which act upon fasteners or clips, such as ligating clips, to close the fasteners or clips about tissue, such as a blood vessel. During the initial closure of the legs of the clip, the clip legs offer little resistance as they move from the fully open position toward the closed position. This low resistance condition occurs over a major portion of the total travel of the clip legs. Thus, it is desirable to provide a jaw closure device in which the output speed at the jaws is greater than the input speed at the operating lever. Because the ligating clip legs offer only a little resistance during the initial part of the closing cycle, the reduced output force at the jaws is not a disadvantage.

Figure 3:
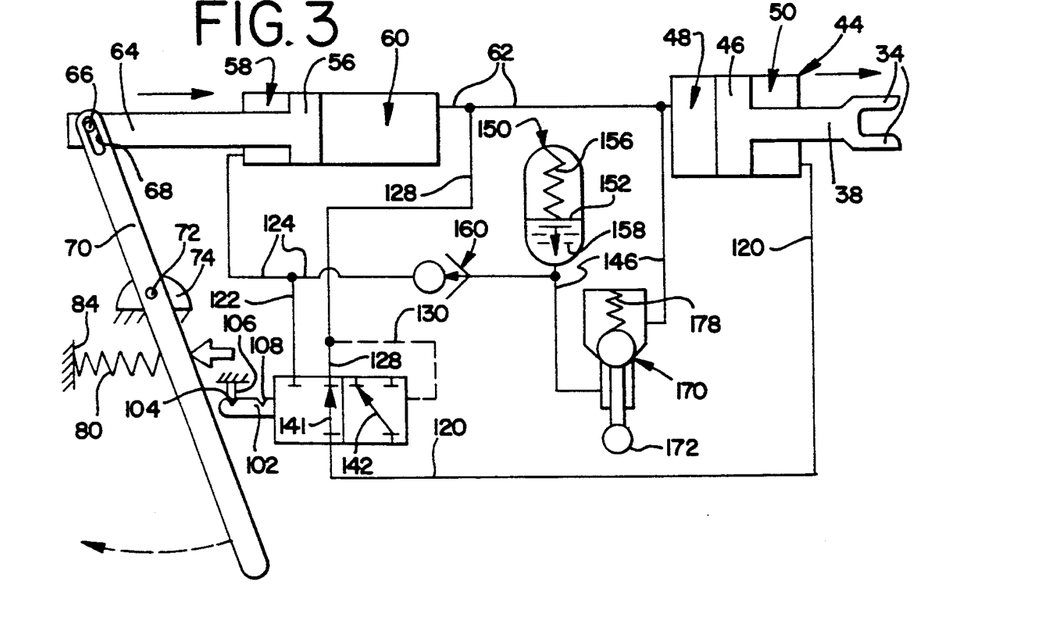

When the system is operated as illustrated in FIG. 2, the pump piston 56 moves along the pump 54, and the actuator piston 46 moves along the actuator 44. As illustrated in FIG. 3, when the pump piston 56 is moved forwardly, the volume of the pump return chamber 58 increases. Hydraulic fluid can flow into the return chamber 58 from the lightly pressurized reservoir 150 through the check valve 160 as illustrated in FIG. 3.

During the operation of some instruments, the last portion of the stroke encounters greater resistance. This is typically the case with ligating clip applier instruments wherein the force required to deform a clip to a fully closed position about tissue increases as the distance between the distal ends of the clip legs decreases. This increased resistance must be overcome by the system if further jaw closure, and hence clip closure, is to be effected. Accordingly, greater force must be applied to the operating lever during the last portion of the stroke.

This increases the pressure in the pump pressurizing chamber 60 and in the actuator extension chamber 48. The increased pressure is transmitted through line 128 to the pilot line 130. When the pressure in the pilot line 130 has increased sufficiently, the force maintained by detent control system (tooth 106 engaged with notch 104 of the valve 100) is exceeded, and the valve 100 automatically shifts to the second position (FIG. 4). This typically occurs when the pump piston 56 is at some intermediate position along the length of the pump 54.

When the directional valve 100 shifts to the second position as illustrated in FIG. 4, the detent control system tooth 106 is received in the notch 108 of the valve stem 102 to maintain the valve 100 in the second position.

When the valve 100 is in the second position as illustrated in FIG. 4, the actuator retraction chamber 50 no longer communicates through the line 120 and valve 100 to the line 128. Thus, the communication between the actuator retraction chamber 50 and the actuator extension chamber 48 and pump pressurizing chamber 60 is terminated. Instead, the actuator retraction chamber 50 communicates through line 120 and valve 100 to line 122 which is connected to line 124 extending to the pump return chamber 58.

If the actuators 44 and 54 have the same piston and rod areas as in the earlier example described above, then the output speed of the actuator rod 38 will decrease but the output force will increase. Specifically, if the lever 70 is still pulled in the clockwise direction at a rate of 1 in./second, then the actuator output speed will be (1 in./second×2 in.$^2$)/3 in.$^2$=0.667 in./second, and this speed is two-thirds of the speed of movement of the pump piston 56.

If the lever 70 is still pulled with a 100 lb. force, the force of the actuator output rod 38 will be (100 lb./2 in.$^2$)×3 in.$^2$=150 lb. This is 1.5 times the 100 lb. pump input force and is 2.73 times the 55 lb. output force of the actuator output rod 38 in the first mode (FIGS. 2 and 3) when the valve 100 was in the first position. The operating mode with lower speed, but higher output force functions effectively to complete the closure of the ligating clip legs.

FIG. 4 illustrates the system as it continues to operate in the higher force mode with the valve 100 in the second position. The pump piston 56 continues moving further toward the right-hand end of the pump 54, and the actuator piston 46 continues moving further toward the right-hand end of the actuator 44. In this mode, the check valve 160 prevents flow from the directional valve 100 into the reservoir 150.

It should be noted that the pump 54 and actuator 44 are sized so that the chambers on each side of each piston define a selected ratio for proper operation. Specifically, the flow rate of the hydraulic fluid out of the actuator retraction chamber 50 is slightly lower than the flow rate required to keep the pump return chamber 58 filled during the movement of the pump piston 56 to the right. This avoids potential hydraulic lock which could occur if more fluid was coming out of the actuator retraction chamber 50 than could flow into the pump return chamber 58. In order to prevent pulling a vacuum in the pump return chamber 58, the check valve 160 will unseat and make-up fluid will flow from the reservoir 150 into the pump return chamber 58.

With some instrument operations, as when closing a ligating clip, it is desirable to prevent the ligating jaws from opening prior to crimping or latching the ligating clip legs completely closed. This could occur if the instrument operator inadvertently lowered the input force applied to the lever 70. For example, if the lever 70 is released, then the return spring 80 will impose a load on the pump rod 64 to pull the pump piston 56 back toward the initial position (toward the left as viewed in FIG. 5).

The pump 54 and actuator 44 are sized so as to impose a hydraulic lock on the system and prevent return of the pistons 56 and 46 toward the initial position so long as the de-stroking valve 170 remains closed. In particular, referring to the component sizes set forth in the earlier example discussed above, if the spring 80 were to move the lever 70 in the counterclockwise direction (as viewed in FIG. 4) to pull the pump piston 56 toward the left at a rate of 1 in./second, then the fluid flow out of the pump return chamber 58 would be 1 in.-/second $\times$ 1.333 in.$^2$ = 1.333 in.$^3$/second. This flow from the pump return chamber 58 would have to pass through line 124, line 122, valve passage 142, and line 120 to the actuator retraction chamber 50. If the entire flow rate from the pump return chamber 58 could be accommodated by the actuator retraction chamber 50, then the return speed of the actuator piston 46 (toward the left in FIG. 4) would be (1.333 in.$^3$/second)/1.9 in.$^2$ = (−)0.702 in./second. The (−)0.702 in./second speed of the piston 46 in the actuator 44 would result in a fluid flow out of the actuator extension chamber 48 of 0.702 in./second $\times$ 3 in.$^2$ = 2.106 in.$^3$/second, and this would be directed into the line 62 connected to the pump pressurizing chamber 60. A flow rate of 2.106 in.$^3$/second into the pump pressurizing chamber 60 would cause the pump piston 56 to move at a speed of (2.106 in.$^3$/seconds)/2 in.$^2$ = 1.053 in./second. Because the actuator piston 46 would thus be attempting to force more fluid into the pump pressurizing chamber 60 than it could accept, hydraulic lock will occur. This prevents return of the actuator rod 38 and prevents premature opening of the jaws engaged by the rod cam channel 34. The system of the present invention is arranged to prevent such inadvertent opening of the jaws so long as the de-stroking valve 170 remains in the closed position as illustrated in FIGS. 1–4.

If it is desired to return the actuator to the initial position upon reaching the end of the stroke, or if it is desired to return the actuator 44 to the initial position before the end of the stroke has been reached, then the de-stroking valve 170 can be opened as illustrated in FIG. 5. When the de-stroking valve 170 is opened (as by pushing the operating lever or handle 172 inwardly), the fluid in the actuator extension chamber 48 can flow through the line 146 to the reservoir 150 (as well as through the line 62 to the pump pressurizing chamber 60). Thus, the excess flow is accumulated in the reservoir 150.

As the pistons 46 and 56 return to the initial positions, the lever 70 is pivoted further counterclockwise by the spring 80 so that the lever 70 eventually engages the distal end of the valve stem 102. This shifts the valve 100 back to the first position (FIGS. 1–3). The de-stroking valve 170 can next be released so that it returns to the closed position. The system is then ready for another actuation cycle.

ALTERNATE EMBODIMENTS

It will be appreciated that the operating lever 70 and compression spring 80 could be eliminated and replaced by other suitable components. For example, a tension spring could be employed to pull the pump piston rod 64 toward the left (as viewed in FIG. 2). The directional valve 100 could be relocated and arranged to be engaged by a portion of the rod 64. The rod 64 could be provided with a suitable portion or surface functioning as an operating member which could be pushed by the surgeon to effect movement of the pump piston 56.

FIGS. 6 and 7, FIGS. 8 and 9, and FIGS. 10 and 11 illustrate other embodiments of the invention wherein the two-position, directional valve is not pilot actuated. Rather, the directional valve is actuated from the first position to the second position, and then from the second position to the first position purely by mechanical engagement with the moving components in the system.

Figure 6:
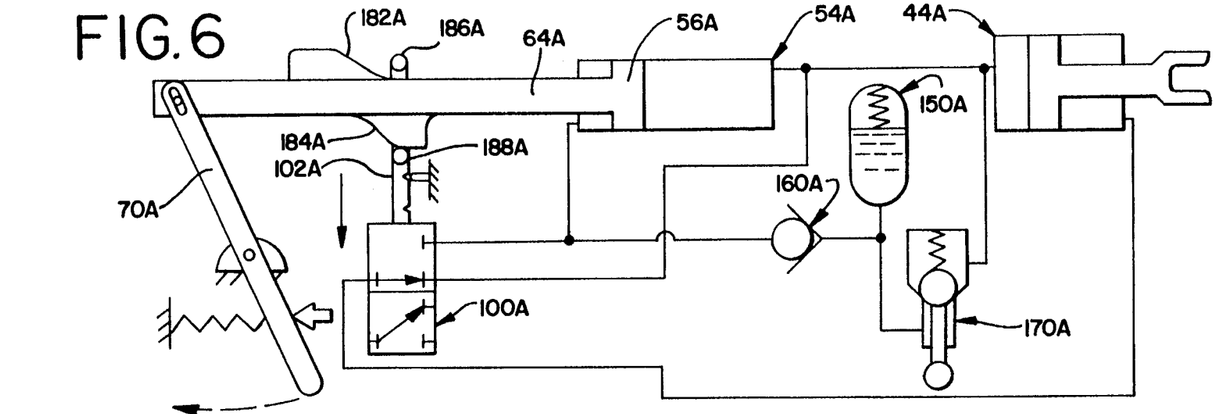
FIG. 6 is a schematic diagram of a second embodiment of the fluid actuation system.
Figure 7:
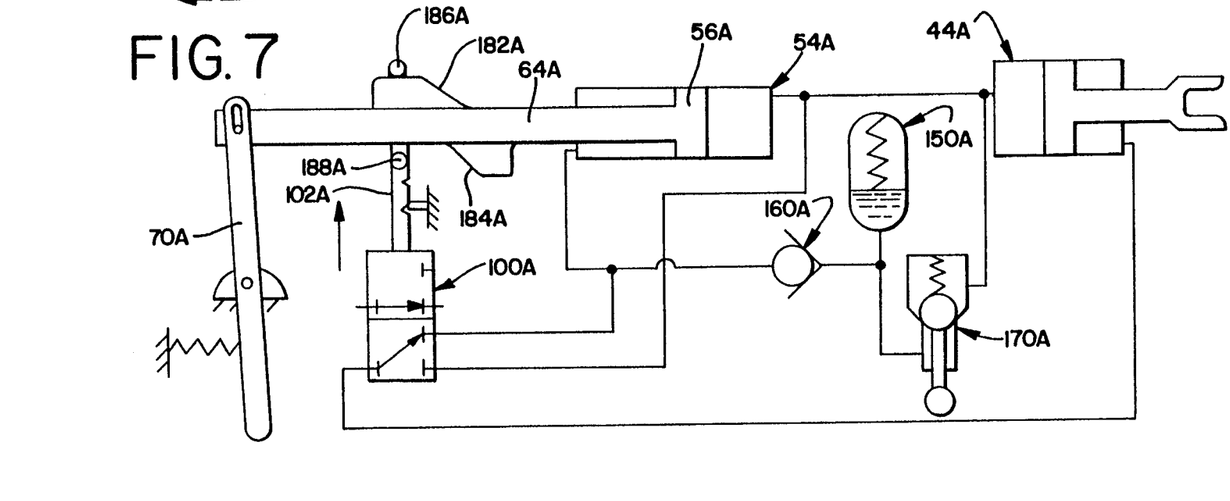
FIG. 7 is a schematic diagram of the second embodiment of the fluid actuation system illustrated in FIG. 6, but FIG. 7 shows the system in a different mode or part of the operation cycle.

In the embodiment illustrated in FIGS. 6 and 7, a double-acting fluid pressure piston pump 54A includes a piston 56A connected to an outwardly projecting piston rod 64A having an upwardly facing cam surface 182A and a downwardly facing cam surface 184A.

A two-position, directional valve 100A, which is not actuated by system pressure through a pilot line, is provided with an operating stem 102A having a pair of spaced-apart, laterally projecting cam followers in the form of an upper cam follower rod 186A and a lower cam follower rod 188A. Except for the cam follower rods 186A and 188A and the lack of a pilot actuation line, the valve 100A is identical to the valve 100 described above with reference to the first embodiment illustrated in FIGS. 1–5.

In the initial, rest position illustrated in FIG. 6, the pump piston rod lower cam surface 184A holds the valve 100A in the first position, and the system can be operated through an initial portion of the stroke by pulling on a lever 70A attached to the piston rod 64A. This effects operation of a double-acting actuator 44A identical to the first embodiment actuator described above with reference to FIGS. 1–5.

The system also includes a pressurized reservoir 150A, check valve 160A, and de-stroking valve 170A. These components are connected, along with the directional valve 100A, pump 54A, and actuator 44A, with lines in the same manner as described above with respect to the first embodiment components 44, 54, 100, 150, 160, and 170 illustrated in FIGS. 1–5. The system operates with the valve 100A in the first position in substantially the same manner as described above with respect to the first mode of operation of the first embodiment of the invention as illustrated in FIGS. 2 and 3.

As the actuator 44A encounters increased resistance, it is desirable to shift the operation to a greater output force mode. In some applications, as when closing ligating clips, the increased resistance will become significant at some point or region along the length of the stroke. This region can be identified by experiment, and the instrument can be designed so that the upper cam surface 182A is located to engage the valve upper cam follower rod 186A at that region of the stroke as shown in FIG. 7. This shifts the valve 100A to the second position. With the valve 100A shifted to the second position, the system operates in the higher output force mode in a manner substantially identical to that described above for the higher output mode operation of the first embodiment as illustrated in FIGS. 4 and 5.

Figure 8:
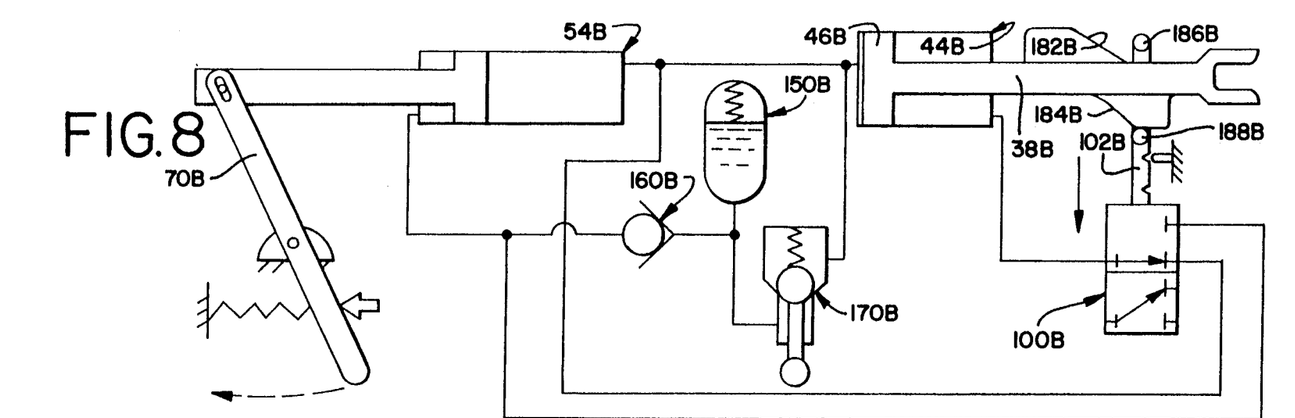
FIG. 8 is a schematic diagram of a third embodiment of the fluid actuation system.
Figure 9:
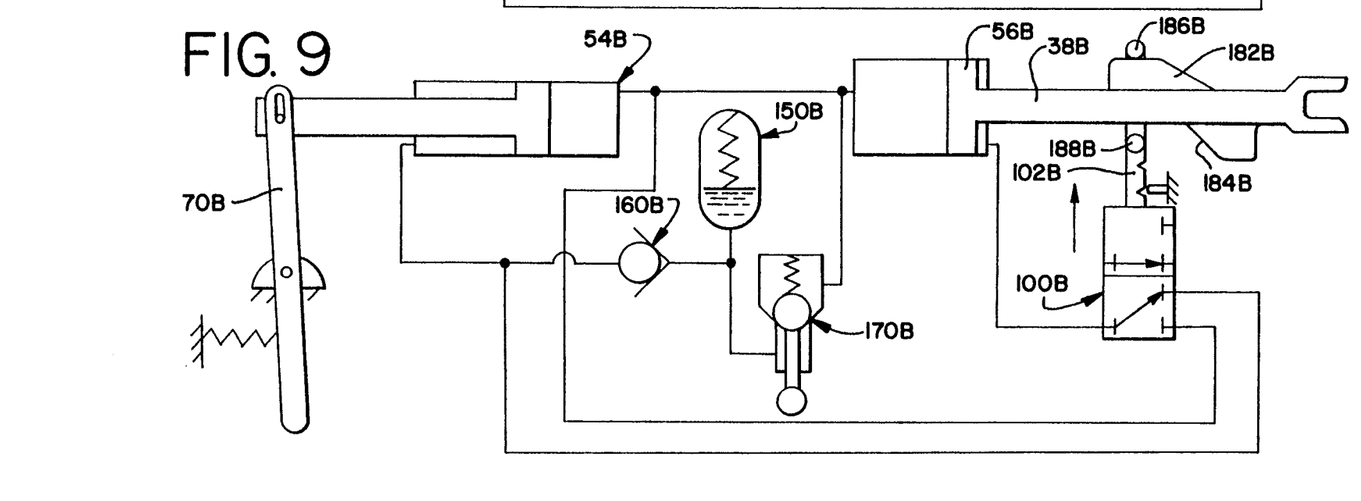
FIG. 9 is a schematic diagram of the third embodiment of the fluid actuation system illustrated in FIG. 8, but FIG. 9 shows the system in a different mode or part of the operation cycle.

FIGS. 8 and 9 illustrate another embodiment of the actuation system using a directional valve 100B that is not actuated by system pressure through a pilot line. The valve 100B is arranged to be mechanically actuated by movement of the rod 38B extending from the piston 46B of the actuator 44B. To this end, the valve 100B has an operating stem 102B with a laterally projecting upper cam follower rod 186B and with a laterally projecting lower cam follower rod 188B. The actuator rod 38B defines an upwardly projecting cam surface 182B and a downwardly projecting cam surface 184B. The system includes a pump 54B, lever 70B, reservoir 150B, check valve 160B, and de-stroking valve 170B. The components are connected with hydraulic lines in a manner identical to that described above with respect to the embodiment illustrated in FIGS. 6 and 7, albeit the valve 100B is in a different location compared to the valve 100A.

The system illustrated in FIGS. 8 and 9 functions in a manner generally analogous to the embodiment of the system described above with reference to FIGS. 6 and 7. In the system illustrated in FIGS. 8 and 9 the upper cam surface 182B is located along the actuator rod 38B at a location generally corresponding to the region of the instrument stroke length at which the higher output force is desired. Thus, when the cam surface 182B engages the cam follower rod 186B, the valve 100B shifts to the second position illustrated in FIG. 9 so that the actuator piston 56B is moved outwardly with a greater force, albeit at a lower speed.

Figure 10:
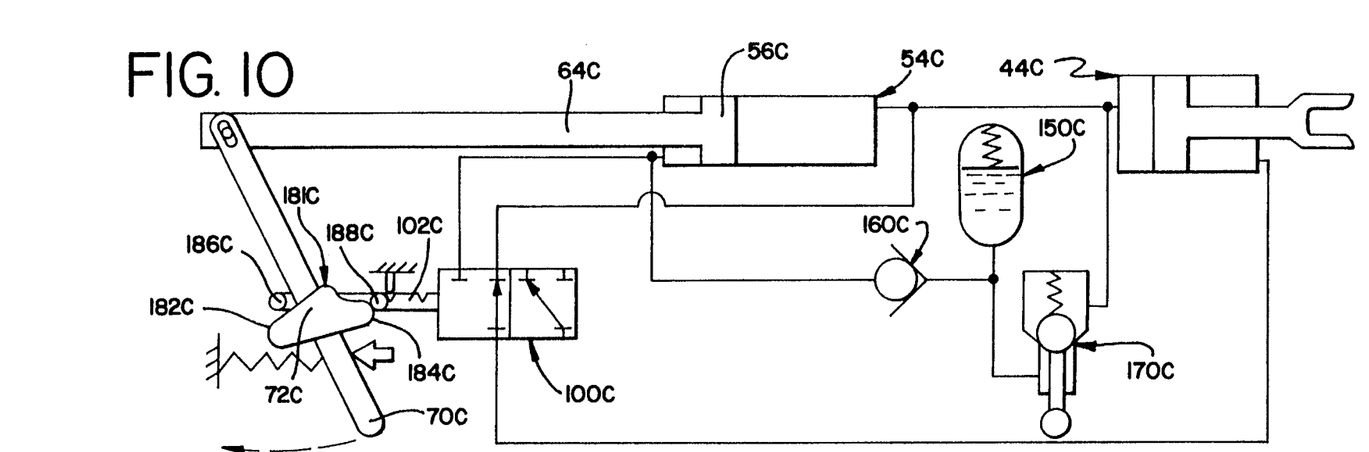
FIG. 10 is a schematic diagram of a fourth embodiment of the fluid actuation system.
Figure 11:
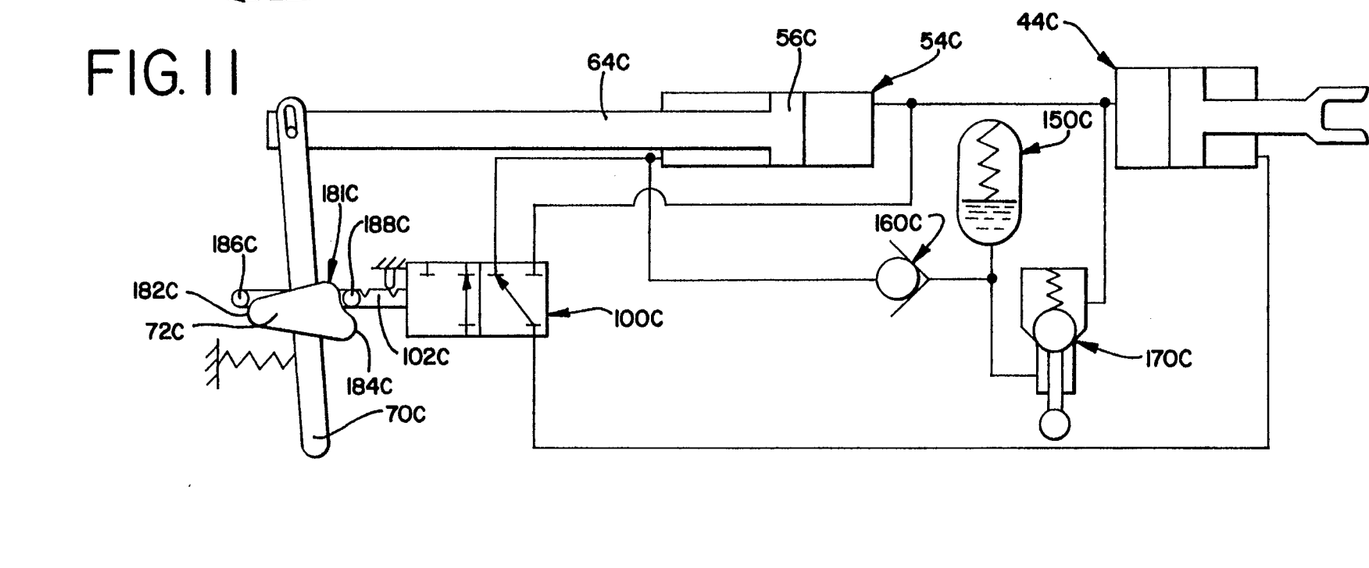
FIG. 11 is a schematic diagram of the fourth embodiment of the fluid actuation system illustrated in FIG. 10, but FIG. 11 shows the system in a different mode or part of the operation cycle.

Yet another embodiment of the actuation system of the present invention is illustrated in FIGS. 10 and 11. This system also employs a two-position, directional valve 100C which is mechanically shifted between two positions and which is not actuated by fluid pressure through a pilot line. The system also includes a pump 54C, actuator 44C, reservoir 150C, check valve 160C, and de-stroking valve 170C. These components are connected with lines in a hydraulic circuit in a manner identical to that described above for the embodiment illustrated in FIGS. 6 and 7.

The pump 54C includes a piston 56C having a projecting piston rod 64C. The lever 70C is connected to the piston rod 64C. The lever 70C pivots about a fixed shaft 72C. The lever 70C includes a cam element 181C which defines a first cam surface 182C and a second cam surface 184C. These cam surfaces are spaced-apart at generally opposite ends of the cam element 181C. The cam element 181C is fixed to the lever 70C so that it rotates with the lever 70C on shaft 72C.

The directional valve 100C has an outwardly projecting operating stem 102C which carries a laterally extending first cam follower rod 186C and a second laterally extending cam follower rod 188C.

In the initial, unactuated condition of the instrument, the lever 70C is biased to engage the cam surface 184C with the cam follower rod 188C to maintain the valve 100C in the first position illustrated in FIG. 10. When the lever 70C is pulled (clockwise as viewed in FIG. 10), the system operates at relatively high speed but low pressure in the same manner as described above for the first mode of operation of the first embodiment illustrated with reference to FIGS. 2–3.

At a region along the length of the stroke where a higher force is desired, the cam surface 182C is tilted upwardly as the cam element 181C pivots with the lever 70C. The cam surface 182C then engages the cam follower rod 186C and shifts the valve 100C to the second position wherein the system operates with higher force at the output of the actuator 44C, albeit at a lower speed.

It will be appreciated that the present invention may be incorporated in a variety of embodiments, such as those described above. The actuation system provides a double-acting actuator operation, and this eliminates the need for return springs in an actuator. This can accommodate the use relatively long stroke actuators which might otherwise be impractical with spring-return actuators.

The actuation system also allows the operator to terminate the stroking process at any point and return the system to an initial condition. However, the system operation cannot be inadvertently returned to the initial condition, and this provides a desirable safety feature.

The actuation system operation can be designed or tailored to the force and stroke requirements of a particular application, such as applying ligating clips. The clip jaw closure duty cycle can also be more efficiently accommodated making it possible to apply multiple clips simultaneously.

It will be readily apparent from the foregoing detailed description of the invention and from the illustrations thereof that numerous variations and modifications may be effected without departing from the true spirit and scope of the novel concepts or principles of this invention.

What is claimed is:

1. A pressurized fluid actuation system suitable for moving an endoscopic or open surgical procedure instrument component, said system comprising:

a double-acting fluid actuator defining an extension chamber and a retraction chamber separated by a piston for engaging said component;

a double-acting fluid pressure piston pump defining a pressurizing chamber and a return chamber separated by a piston, said actuator extension chamber communicating with said pump pressurizing chamber;

an operating member connected to said pump piston;

a two-position, directional valve communicating in a first position between said pump pressurizing chamber and said actuator retraction chamber and communicating in a second position between said pump return chamber and said actuator retraction chamber, said directional valve including a pilot line communicating with said pump pressurizing chamber for switching said valve from said first position to said second position when said pressurizing chamber pressure exceeds a predetermined value, and said operating member located to engage said directional valve and move said valve from said second position to said first position; and a pressurized fluid reservoir connected to (A) said pump return chamber through a check valve preventing flow through said check valve into said reservoir and (B) said actuator extension chamber through a de-stroking valve having a selectable open position to pass flow through it to said reservoir and having a selectable closed position to occlude said flow.

2. The actuation system in accordance with claim 1 in which
said system includes hydraulic liquid;

said pump has a housing in which said pump piston is slidably disposed; and said actuator has a housing in which said actuator piston is slidably disposed.

3. The actuation system in accordance with claim 1 in which said actuator piston includes a piston rod which projects through an end of said housing and which is connected to said instrument component.

4. The actuation system in accordance with claim 1 in which said pump piston includes a piston rod which projects through an end of said housing;

said operating member is a pivotally mounted lever and said piston rod is pivotally connected to said lever.

5. The actuation system in accordance with claim 1 in which said operating member is a lever; and said system further includes a spring for biasing said lever into engagement with said directional valve to urge said directional valve to said first position.

6. The actuation system in accordance with claim 1 in which said directional valve includes a detent control to hold said valve alternately in each of said first and second positions with a predetermined force.

7. The actuation system in accordance with claim 1 in which said operating member is a lever which is connected to said pump piston at a first location and which is pivotally mounted to said instrument at a second location for pivoting through a range of motion at a location adjacent said directional valve.

8. A pressurized fluid actuation system suitable for moving an endoscopic or open surgical procedure instrument component, said system comprising:

a double-acting fluid actuator defining an extension chamber and a retraction chamber separated by a piston for engaging said component;

a double-acting fluid pressure piston pump defining a pressurizing chamber and a return chamber separated by a piston, said actuator extension chamber being connected to said pump pressurizing chamber;

an operating lever pivotally mounted to said piston at a first location and pivotally mounted to said instrument at a second location for pivoting through a range of motion at a location adjacent said directional valve;

a directional valve having (a) a connection to said actuator retraction chamber, (b) a connection to said pump return chamber, (c) a connection to said pump pressurizing chamber, and (d) a pilot connection to said pump pressurizing chamber for switching said valve when said pump pressurizing chamber pressure exceeds a predetermined value from a first position establishing communication between said pump pressurizing chamber and said actuator retraction chamber to a second position establishing communication between said pump return chamber and said actuator retraction chamber, said operating lever located to engage said valve and move said valve from said second position to said first position when said lever is pivoted to one extreme of its range of movement;

a pressurized fluid reservoir connected to said pump return chamber through a check valve preventing flow through said check valve into said reservoir and permitting flow from said reservoir through said check valve; and a de-stroking valve connected between said reservoir and said actuator extension chamber, said de-stroking valve having a selectable closed position occluding flow between said reservoir and said actuator extension chamber and having a selectable open position permitting flow from said actuator extension chamber into said reservoir.

9. A pressurized fluid actuation system suitable for moving an endoscopic or open surgical procedure instrument component, said system comprising:

a double-acting fluid actuator defining an extension chamber and a retraction chamber separated by a piston for engaging said component;

a double-acting fluid pressure piston pump defining a pressurizing chamber and a return chamber separated by a piston, said actuator extension chamber communicating with said pump pressurizing chamber;

an operating member connected to said pump piston;

a two-position, directional valve communicating in a first position between said pump pressurizing chamber and said actuator retraction chamber and communicating in a second position between said pump return chamber and said actuator retraction chamber;

valve actuation means responsive to the position of one of said pump piston and said actuator piston for switching said valve from (a) said first position to said second position when said one piston has moved to an intermediate location, and (b) said second position to said first position when said one piston has returned from said intermediate position; and a pressurized fluid reservoir connected to (A) said pump return chamber through a check valve preventing flow through said check valve into said reservoir and (B) said actuator extension chamber through a de-stroking valve having a selectable open position to pass flow through it to said reservoir and having a selectable closed position to occlude said flow.

10. The actuation system in accordance with claim 9 in which said directional valve includes a valve stem having a projecting end;

said operating member includes a rod that extends from said pump piston; and said valve actuation means includes (a) two spaced-apart, oppositely projecting cam surfaces defined on one of said rod and valve stem end, and (b) two spaced-apart cam followers defined on the other of said rod and said valve stem end for each being engaged by one of said cam surfaces.

11. The actuation system in accordance with claim 9 in which said operating member is a multiple piece assembly that includes a rod extending from said pump piston and a lever pivotally mounted to said rod;

said directional valve is pilot-actuated; and said vane actuation means includes (a) a pilot line communicating with said pump pressurizing chamber for switching said vane from said first position to said second position when said pump piston has moved to said intermediate location in said pump while said pressurizing chamber pressure exceeds a predetermined value, and (b) a valve stem having a projecting end engaged by said lever when said pump piston has returned from said intermediate position whereby said valve is switched from said second position to said first position.

12. The actuation system in accordance with claim 9 in which said directional vane includes a valve stem having a projecting end;

said operating member is a multiple piece assembly that includes a rod extending from said pump piston and a lever pivotally attached to said rod; and said valve actuation means includes (a) two spaced-apart, oppositely projecting cam surfaces defined on one of said lever said valve stem end, and (b) two spaced-apart cam followers defined on the other of said lever and said valve stem end for each being engaged by one of said cam surfaces.

13. The actuation system in accordance with claim 9 in which said directional vane includes a valve stem having a projecting end;

said double-acting fluid actuator includes a drive rod projecting from said actuator piston; and said valve actuation means includes (a) two spaced-apart, oppositely projecting cam surfaces defined on one of said drive rod and said valve stem end, and (b) two spaced-apart cam followers defined on the other of said drive rod and said valve stem end for each being engaged by one of said cam surfaces.

* * * * *